United States Patent
Rickard et al.

(10) Patent No.: US 8,721,580 B2
(45) Date of Patent: May 13, 2014

(54) POWER SAVING GLAUCOMA DRAINAGE DEVICE

(75) Inventors: Matthew J. A. Rickard, Tustin, CA (US); Robert Joseph Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 185 days.

(21) Appl. No.: 12/837,803

(22) Filed: Jul. 16, 2010

(65) Prior Publication Data

US 2011/0071459 A1    Mar. 24, 2011

Related U.S. Application Data

(63) Continuation-in-part of application No. 12/685,772, filed on Jan. 12, 2010, now abandoned, which is a continuation-in-part of application No. 12/609,043, filed on Oct. 30, 2009, now Pat. No. 8,545,431, which is a continuation-in-part of application No. 12/563,244, filed on Sep. 21, 2009, now Pat. No. 8,257,295.

(51) Int. Cl.
*A61B 3/16* (2006.01)

(52) U.S. Cl.
USPC ............... 604/9; 600/398; 600/399; 600/405

(58) Field of Classification Search
USPC ............... 600/398, 561; 604/9, 540; 623/4.1; 128/903
See application file for complete search history.

(56) References Cited

U.S. PATENT DOCUMENTS

| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters et al. |

(Continued)

FOREIGN PATENT DOCUMENTS

| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Leslie R. Deak
*Assistant Examiner* — Sara Sass
(74) *Attorney, Agent, or Firm* — Kenneth D. Bassinger

(57) ABSTRACT

A glaucoma drainage device has an active valve configured to be located between an anterior chamber of an eye and a drainage location, a power source coupled to the active valve, and a controller coupled to the power source. A first pressure sensor is located in fluid communication with the anterior chamber, a second pressure sensor is located in the drainage location, and a third pressure sensor located remotely from the first and second pressure sensors. The controller reads the first, second, and third pressure sensors once during a period of time and adjusts the active valve to control intraocular pressure.

8 Claims, 11 Drawing Sheets

(56) References Cited

U.S. PATENT DOCUMENTS

| | | | |
|---|---|---|---|
| 5,005,577 | A | 4/1991 | Frenkel |
| 5,083,742 | A | 1/1992 | Wylie et al. |
| 5,178,604 | A | 1/1993 | Baerveldt |
| 5,179,953 | A | 1/1993 | Kursar |
| 5,397,300 | A | 3/1995 | Baerveldt |
| 5,466,233 | A | 11/1995 | Weiner et al. |
| 5,476,445 | A | 12/1995 | Baerveldt |
| 5,558,629 | A | 9/1996 | Baerveldt |
| 5,707,643 | A | 1/1998 | Ogura et al. |
| 5,910,110 | A * | 6/1999 | Bastable ............... 600/398 |
| 6,007,511 | A | 12/1999 | Prywes |
| 6,048,328 | A | 4/2000 | Haller et al. |
| 6,251,090 | B1 | 6/2001 | Avery et al. |
| 6,447,449 | B1 | 9/2002 | Fleischman et al. |
| 6,468,283 | B1 | 10/2002 | Richter et al. |
| 6,579,235 | B1 | 6/2003 | Abita et al. |
| 6,589,198 | B1 | 7/2003 | Soltanpour et al. |
| 6,682,500 | B2 | 1/2004 | Soltanpour et al. |
| 6,712,764 | B2 | 3/2004 | Jeffries et al. |
| 6,719,750 | B2 | 4/2004 | Varner et al. |
| 6,749,568 | B2 | 6/2004 | Fleischman et al. |
| 6,939,299 | B1 | 9/2005 | Petersen et al. |
| 6,976,982 | B2 | 12/2005 | Santini et al. |
| 7,137,952 | B2 | 11/2006 | Leonardi et al. |
| 7,169,106 | B2 | 1/2007 | Fleischman et al. |
| 7,252,006 | B2 | 8/2007 | Tai et al. |
| 7,354,416 | B2 | 4/2008 | Quiroz-Mercado et al. |
| 7,409,863 | B2 | 8/2008 | Bateman et al. |
| 7,612,328 | B2 | 11/2009 | Kaiser |
| 7,756,559 | B2 | 7/2010 | Abreu |
| 8,182,435 | B2 | 5/2012 | Dacquay et al. |
| 8,257,295 | B2 | 9/2012 | Rickard et al. |
| 8,419,673 | B2 | 4/2013 | Rickard |
| 2001/0000527 | A1 | 4/2001 | Yaron et al. |
| 2002/0019607 | A1* | 2/2002 | Bui ............... 604/67 |
| 2002/0049374 | A1 | 4/2002 | Abrea |
| 2002/0099359 | A1 | 7/2002 | Santini, Jr. et al. |
| 2002/0139947 | A1 | 10/2002 | Wang |
| 2002/0143284 | A1 | 10/2002 | Tu et al. |
| 2002/0193674 | A1 | 12/2002 | Fleischman et al. |
| 2003/0014036 | A1 | 1/2003 | Varner et al. |
| 2003/0078487 | A1 | 4/2003 | Jeffries et al. |
| 2003/0225318 | A1 | 12/2003 | Montegrande et al. |
| 2004/0059248 | A1 | 3/2004 | Messner et al. |
| 2004/0073137 | A1 | 4/2004 | Lloyd et al. |
| 2004/0111050 | A1 | 6/2004 | Smedley et al. |
| 2004/0116794 | A1 | 6/2004 | Fink et al. |
| 2004/0186367 | A1* | 9/2004 | Fresco ............... 600/398 |
| 2004/0254438 | A1 | 12/2004 | Chuck et al. |
| 2004/0254517 | A1 | 12/2004 | Quiroz-Mercado et al. |
| 2005/0049578 | A1 | 3/2005 | Tu et al. |
| 2005/0159660 | A1 | 7/2005 | Montegrande et al. |
| 2005/0271704 | A1 | 12/2005 | Tu et al. |
| 2005/0273033 | A1 | 12/2005 | Grahn et al. |
| 2006/0131350 | A1 | 6/2006 | Schechter et al. |
| 2007/0019156 | A1* | 1/2007 | Fink ............... 351/200 |
| 2007/0032757 | A1* | 2/2007 | Medow et al. ............... 604/9 |
| 2007/0077270 | A1 | 4/2007 | Wen |
| 2007/0106199 | A1 | 5/2007 | Krivoy et al. |
| 2007/0109117 | A1 | 5/2007 | Heitzmann et al. |
| 2007/0123767 | A1 | 5/2007 | Montegrande et al. |
| 2007/0129623 | A1 | 6/2007 | Fleischman et al. |
| 2007/0212397 | A1 | 9/2007 | Roth |
| 2008/0015421 | A1 | 1/2008 | Penner |
| 2008/0077127 | A1* | 3/2008 | Gao et al. ............... 606/34 |
| 2008/0097276 | A1 | 4/2008 | Bertrand et al. |
| 2008/0125691 | A1 | 5/2008 | Yaron et al. |
| 2008/0129486 | A1 | 6/2008 | Jeckelmann et al. |
| 2008/0147021 | A1 | 6/2008 | Jani |
| 2008/0228127 | A1 | 9/2008 | Burns et al. |
| 2009/0069648 | A1 | 3/2009 | Irazoqui et al. |
| 2009/0076367 | A1* | 3/2009 | Sit et al. ............... 600/398 |
| 2009/0143713 | A1* | 6/2009 | Van Dam et al. ............... 604/9 |
| 2009/0227933 | A1 | 9/2009 | Karageozian |
| 2009/0240215 | A1 | 9/2009 | Humayun et al. |
| 2009/0275924 | A1* | 11/2009 | Lattanzio et al. ............... 604/891.1 |
| 2009/0312742 | A1 | 12/2009 | Pang et al. |
| 2010/0010416 | A1 | 1/2010 | Juan, Jr. et al. |
| 2010/0042209 | A1* | 2/2010 | Guarnieri ............... 623/4.1 |
| 2010/0121248 | A1 | 5/2010 | Yu et al. |
| 2010/0174272 | A1 | 7/2010 | Weiner |
| 2010/0222769 | A1 | 9/2010 | Meng et al. |
| 2010/0234717 | A1 | 9/2010 | Wismer |
| 2010/0253167 | A1 | 10/2010 | Charnley et al. |
| 2010/0305550 | A1 | 12/2010 | Meng et al. |
| 2011/0046536 | A1* | 2/2011 | Stegmann et al. ............... 604/8 |
| 2011/0071454 | A1 | 3/2011 | Dos Santos et al. |
| 2011/0071456 | A1 | 3/2011 | Rickard |
| 2011/0071505 | A1 | 3/2011 | Rickard et al. |
| 2011/0248671 | A1 | 10/2011 | Dos Santos et al. |

FOREIGN PATENT DOCUMENTS

| | | |
|---|---|---|
| WO | WO 93/03665 A1 | 3/1993 |
| WO | 9803809 | 1/1998 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | 02056758 | 7/2002 |
| WO | WO 03/001991 A1 | 1/2003 |
| WO | WO 03/102632 | 12/2003 |
| WO | 2005088417 | 9/2005 |
| WO | WO 2007/127305 A2 | 11/2007 |
| WO | WO 2007/136993 A1 | 11/2007 |
| WO | WO 2008/061043 A2 | 5/2008 |
| WO | 2008084350 | 7/2008 |
| WO | 2009010799 | 1/2009 |
| WO | WO 2009/026499 A1 | 2/2009 |
| WO | WO 2009/049686 A1 | 4/2009 |
| WO | WO 2009/081031 | 7/2009 |
| WO | WO 2009/081031 A3 | 9/2009 |
| WO | 2010129446 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |
| WO | 2012012017 | 1/2012 |

OTHER PUBLICATIONS

Walter, Peter; "Intraocular Pressure Sensor: Where Are We—Where Will We Go?" Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

(56) References Cited

OTHER PUBLICATIONS

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.
Schnakenberg, U., et al, "Initial Investigations on Systems for Measuring Intraocular Pressure," Sensors and Actuators, 2000, p. 287-291, vol. 85, Elsevier Science B.V., Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
International Searching Authority, Search Report and Written Opinion of the International Searching Authority, PCT/US2010/033329, Jul. 13, 2010, 11 pages.
International Searching Authority, Search Report and Written Opinion of the International Searching Authority, PCT/US2010/047600, Dec. 14, 2010, 11 pages.
International Searching Authority, Search Report and Written Opinion of the International Searching Authority, PCT/US2010/047429, Nov. 1, 2010, 11 pages.
International Searching Authority, Search Report and Written Opinion of the International Searching Authority, PCT/US2010/049424, Nov. 26, 2010, 11 pages.
International Searching Authority, Written Opinion of the International Searching Authority, PCT/US2010/047605, Dec. 16, 2010, 9 pages.
International Searching Authority, Search Report of the International Searching Authority, PCT/US2011/036742, Aug. 17, 2011, 2 pages.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; Trans Am Ophthalmol Soc 2009; 107; pp. 60-71.
Erik Stemme and Goran Stemme; "A Valveless Diffuser/Nozzle-Based Fluid Pump"; ScienceDirect; Sensors and Actuators A, 39 (1993); pp. 159-167.
International Searching Authority, International Search Report of the International Searching Authority, PCT/US2010/047612, Dec. 21, 2010, 7 pages.
International Searching Authority, Written Opinion of the International Searching Authority, PCT/US2010/047612, Dec. 21, 2010, 10 pages.
Driot et al.; "Ocular pharmacokinetics of fluocinolone acetonide after RetisertTM intravitreal implantation in rabbits over a 1-year period"; J. Ocular Pharm; vol. 20; No. 3; pp. 269-275 (2004).
Glybina et al.; "Neuroprotective properties of fluocinolone acetonide chronically delivered into the vitreous of albino RCS rats"; IVOS; vol. 47; ARVO E—Abstract 1028 (2006).
Kupperman et al.; "Efficacy and safety of a novel intravitreous dexamethasone drug-delivery system after applicator or incisional placement in patients with macular edema"; IVOS; vol. 47; ARVO E—Abstract 5913 (2006).
Miyamoto et al.; "Biodegradable scleral implant for intravitreal controlled release of fluconazole"; Current Eye Res.; vol. 16; No. 19; pp. 930-935 (1997).
Miruthyunjaya et al.; "An intravitreal sustained release fluocinolone acetonide device to treat severe experimental uveitis"; IVOS; vol. 44; ARVO E—Abstract 4215 (2003).
Ratanapakorin et al.; "Helical intravitreal triamcinolone implant: An explanation survival study"; IVOS; vol. 46; ARVO E—Abstract 484 (2005).
Rego et al; "In vitro evaluation of sustained-release intravitreal dexamethasone implants"; IVOS; vol. 45; ARVO E—Abstract 5060 (2004).
Sakurai et al.; "Scleral plug of biodegradable polymers containing ganciclovir for experimental cytomegalovirus retinitis"; IVOS; vol. 42; No. 9; pp. 2043-2048 (2004).
See et al.; "Safety and drug release profile of injectable intravitreal sustained-release fluocinolone acetonide device"; IVOS; vol. 47; ARVO E—Abstract 5119 (2006).
Tano et al.; "Helical intravitreal implant: surgical method development and outcomes"; IVOS; vol. 46; ARVO E—Abstract 483 (2005).
Varner et al.; "Development of a minimally invasive intravitreal implant for drug delivery"; IVOS vol. 44; ARVO E—Abstract 4214 (2003).
Weiner; "Drug delivery systems in ophthalmic applications; In Ocular Therapeutics; Eye on New Discoveries; T. Yorio, A. Clark, M. Wax, Eds, Elsevier Press/Academic Press, New York", pp. 7-43 (2007).
Yasukawa et al.; "Biodegradable scleral plugs for vitreoretinal drug delivery"; Adv. Drug Del. Rev.; vol. 52; No. 1; pp. 25-36 (2001).
International Search Report and Written Opinion corresponding to PCT/US2012/068878 dated Apr. 3, 2013.
International Search Report and Written Opinion corresponding to PCT/US2012/067747 dated Apr. 2, 2013.

\* cited by examiner

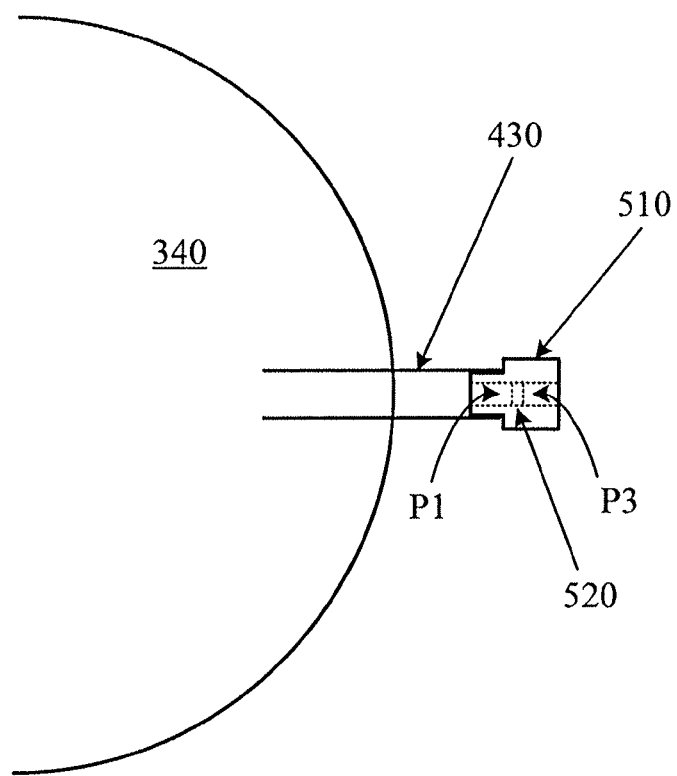
Fig. 5
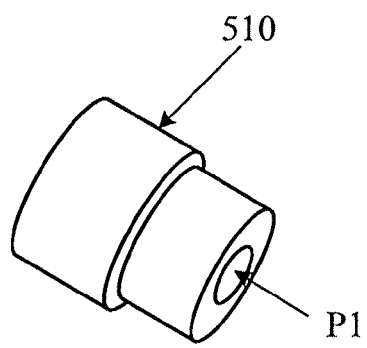 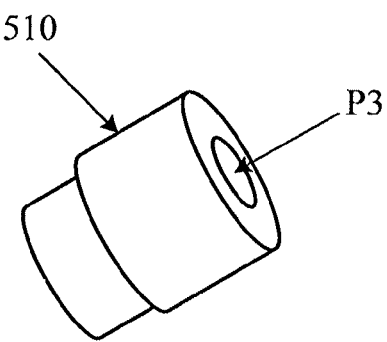
Fig. 6A                Fig. 6B

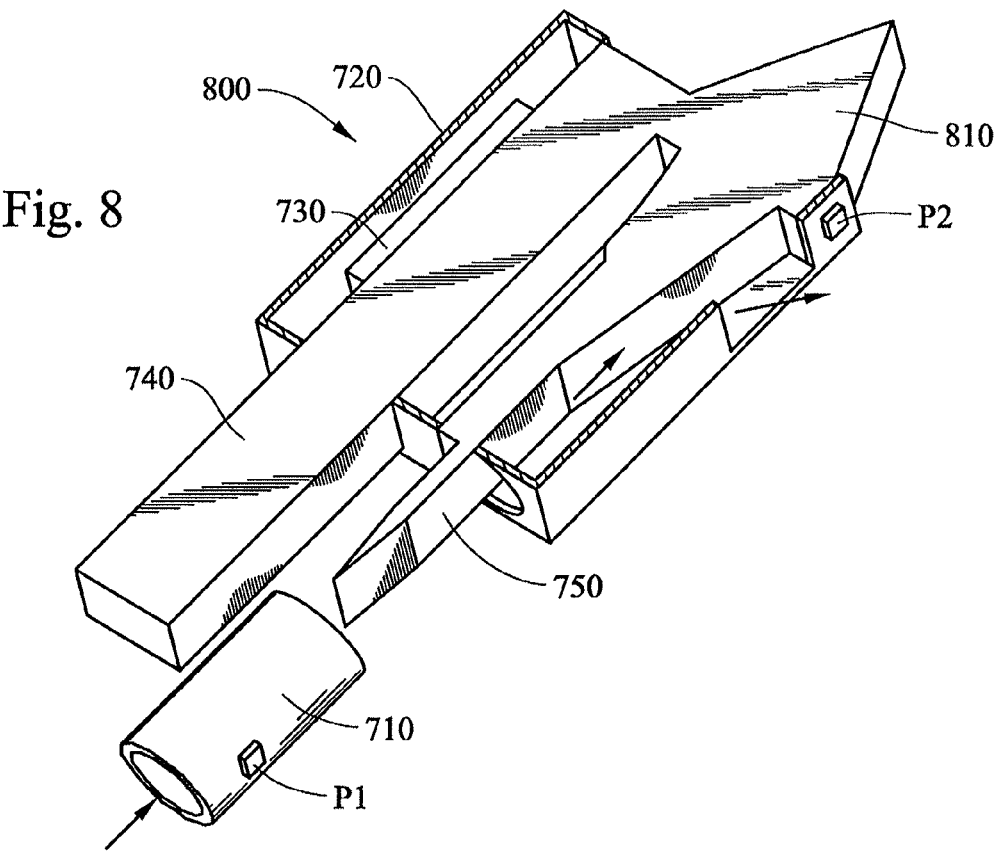
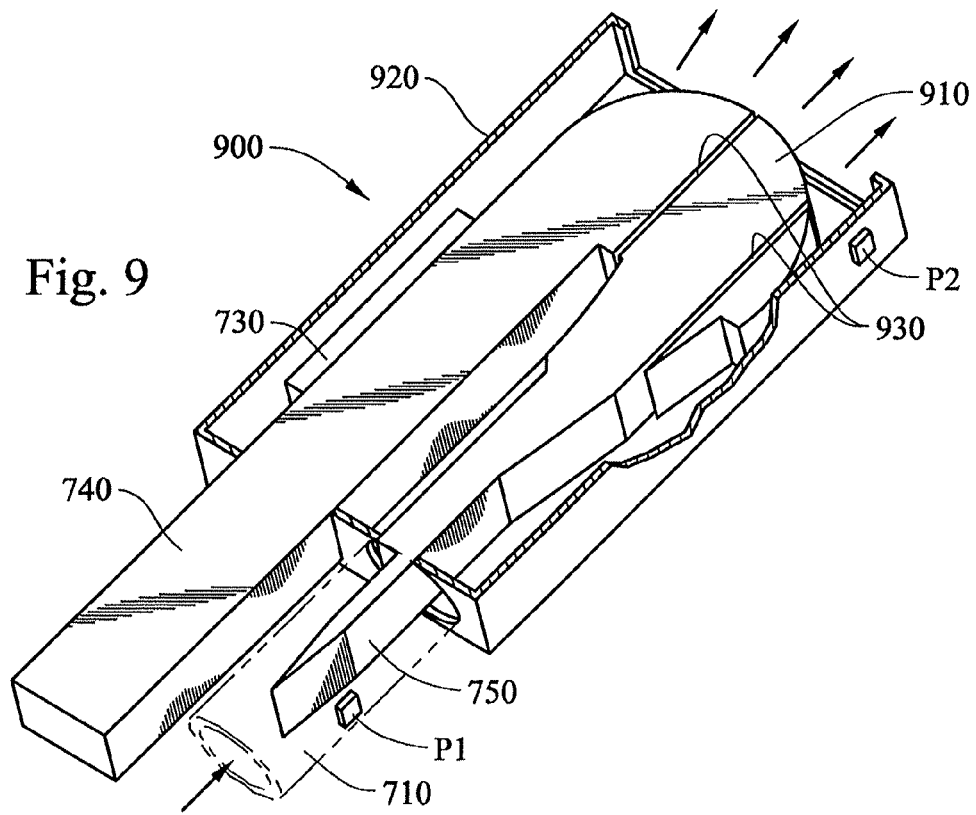

POWER SAVING GLAUCOMA DRAINAGE DEVICE

This application is a continuation-in-part of U.S. application Ser. No. 12/685,772 filed Jan. 12, 2010, which is a continuation-in-part of U.S. application Ser. No. 12/609,043 filed Oct. 30, 2009, which is a continuation-in-part of U.S. application Ser. No. 12/563,244 filed Sep. 21, 2009.

BACKGROUND OF THE INVENTION

The present invention relates to a glaucoma drainage device that is operated so as to conserve power.

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous humor and the drainage of the aqueous humor. Left untreated, an elevated IOP causes irreversible damage the optic nerve and retinal fibers resulting in a progressive, permanent loss of vision.

The eye's ciliary body epithelium constantly produces aqueous humor, the clear fluid that fills the anterior chamber of the eye (the space between the cornea and iris). The aqueous humor flows out of the anterior chamber through the uveoscleral pathways, a complex drainage system. The delicate balance between the production and drainage of aqueous humor determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower the eye pressure. In some cases, surgery is performed if the IOP cannot be adequately controlled with medical therapy.

Only about 10% of the population suffers from acute angle closure glaucoma. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

FIG. 1 is a diagram of the front portion of an eye that helps to explain the processes of glaucoma. In FIG. 1, representations of the lens 110, cornea 120, iris 130, ciliary bodies 140, trabecular meshwork 150, and Schlemm's canal 160 are pictured. Anatomically, the anterior chamber of the eye includes the structures that cause glaucoma. Aqueous fluid is produced by the ciliary bodies 140 that lie beneath the iris 130 and adjacent to the lens 110 in the anterior chamber. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The first structure, and the one most commonly implicated in glaucoma, is the trabecular meshwork 150. The trabecular meshwork 150 extends circumferentially around the anterior chamber in the angle. The trabecular meshwork 150 seems to act as a filter, limiting the outflow of aqueous humor and providing a back pressure producing the IOP. Schlemm's canal 160 is located beyond the trabecular meshwork 150. Schlemm's canal 160 has collector channels that allow aqueous humor to flow out of the anterior chamber. The two arrows in the anterior chamber of FIG. 1 show the flow of aqueous humor from the ciliary bodies 140, over the lens 110, over the iris 130, through the trabecular meshwork 150, and into Schlemm's canal 160 and its collector channels.

In glaucoma patients, IOP can vary widely during a 24 hour period. Generally, IOP is highest in the early morning hours before medication is administered upon waking. Higher pressures damage the optic nerve and can lead to blindness. Accordingly, it would be desirable to have an active glaucoma drainage device that controls IOP.

SUMMARY OF THE INVENTION

In one embodiment consistent with the principles of the present invention, the present invention is a glaucoma drainage device comprising: an active valve configured to be located between an anterior chamber of an eye and a drainage location; a power source coupled to the active valve; and a controller coupled to the power source; wherein the controller directs power from the power source to the active valve based on a pressure.

In another embodiment consistent with the principles of the present invention, the present invention is an intraocular pressure sensor system comprising: a first pressure sensor located in fluid communication with an anterior chamber of an eye; a remote pressure sensor located remotely from the first pressure sensor such that the remote pressure sensor measures or approximates atmospheric pressure; a controller configured to read the first and second pressure sensors; and a power source coupled to the controller; wherein a difference between readings from the first pressure sensor and the remote pressure sensor approximates intraocular pressure; and further wherein the controller reads the first pressure sensor and the second pressure sensor once during a time period.

In another embodiment consistent with the principles of the present invention, the present invention is an intraocular pressure sensor system comprising: a first pressure sensor located in fluid communication with an anterior chamber of an eye; a second pressure sensor located in a drainage location; a controller configured to read the first and second pressure sensors; and a power source coupled to the controller; wherein a difference between readings from the first pressure sensor and the second pressure sensor approximates a pressure differential between the anterior chamber and the drainage location; and further wherein the controller reads the first pressure sensor and the second pressure sensor once during a time period.

In another embodiment consistent with the principles of the present invention, the present invention is an intraocular pressure sensor system comprising: a first pressure sensor located in a drainage location; a remote pressure sensor located remotely from the first pressure sensor such that the remote pressure sensor measures or approximates atmospheric pressure; a controller configured to read the first and second pressure sensors; and a power source coupled to the controller; wherein a difference between readings from the first pressure sensor and the remote pressure sensor approximates pressure in the drainage location; and further wherein the controller reads the first pressure sensor and the second pressure sensor once during a time period.

In another embodiment consistent with the principles of the present invention, the present invention is a glaucoma drainage device comprising: an active valve configured to be located between an anterior chamber of an eye and a drainage location; a power source coupled to the active valve; a controller coupled to the power source; a first pressure sensor located in fluid communication with the anterior chamber; a second pressure sensor located in the drainage location; and a third pressure sensor located remotely from the first and second pressure sensors; wherein the controller reads the first, second, and third pressure sensors once during a period of time.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 5 is an end cap implementation of an IOP sensor consistent with the principles of the present invention.

FIGS. 6A and 6B are perspective views of an end cap implementation of an IOP sensor consistent with the principles of the present invention.

FIG. 8 is a perspective view of a lumen clearing valve with a fiber clearing member according to the principles of the present invention.

FIG. 9 is a perspective view of a lumen clearing valve with an aqueous dispersion member to clear fibrosis according to the principles of the present invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
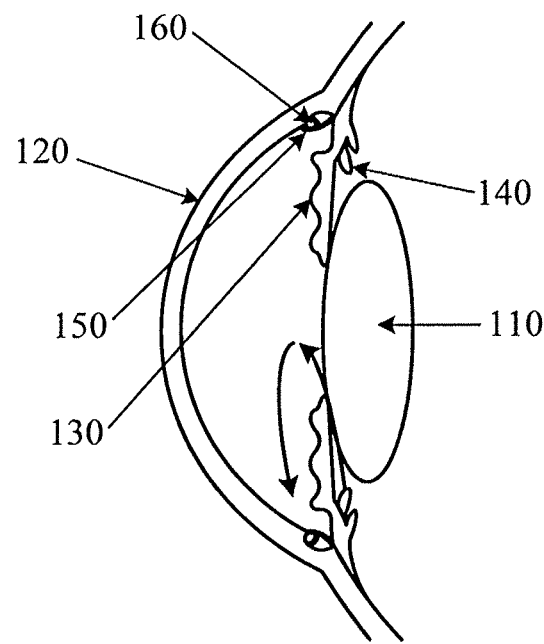
FIG. 1 is a diagram of the front portion of an eye.
Figure 2:
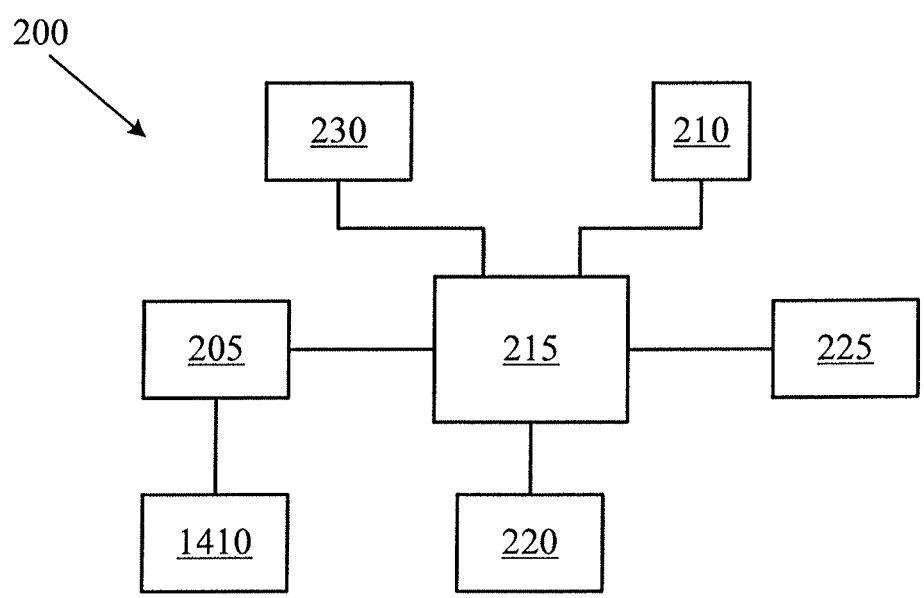
FIG. 2 is a block diagram of an IOP measuring system according to the principles of the present invention.

FIG. 2 is a block diagram of an IOP measuring system 200 according to the principles of the present invention. In FIG. 2, the IOP measuring system includes power source 205, IOP sensor 210 (which can include P1, P2, and/or P3), processor 215, memory 220, data transmission module 225, and optional speaker 230.

Power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via an RFID link or other type of magnetic coupling.

In another embodiment of the present invention, power source 205 is a capacitor that stores charge generated by generator 1410 as explained below. Other types of charge storing or energy storing devices may also be employed to implement power source 205. As more fully explained below, generator 1410 is coupled to power source 205.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, speaker 230, power source 205, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as NAND flash memory. As the size of semiconductor memory is very small, and the memory needs of the system 200 are small, memory 220 occupies a very small footprint of system 200. Memory 220 interfaces with processor 215. As such, processor 215 can write to and read from memory 220. For example, processor 215 can be configured to read data from the IOP sensor 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), and the like.

Optional speaker 230 provides a warning tone or voice to the patient when a dangerous condition exists. For example, if IOP is at a level that is likely to lead to damage or presents a risk to the patient, speaker 230 may sound a warning tone to alert the patient to seek medical attention or to administer eye drops. Processor 215 reads IOP measurements from IOP sensor 210. If processor 215 reads one or a series of IOP measurements that are above a threshold, then processor 215 can operate speaker 230 to sound a warning. The threshold can be set and stored in memory 220. In this manner, an IOP threshold can be set by a doctor, and when exceeded, a warning can be sounded.

Alternatively, data transmission module may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. In this case, the secondary device may contain the speaker 230. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff via speaker 230 or by transmitting the unsafe readings to a secondary device.

Such a system is also suitable for use outside a hospital setting. For example, if an unsafe IOP condition exists, processor 215 can operate speaker 230 to sound an audible warning. The patient is then alerted and can seek medical attention. The warning can be turned off by a medical professional in a number of ways. For example, when data transmission module 225 is an RFID tag, an RFID link can be established between an external device and system 200. This external device can communicate with system 200 to turn off the speaker 230. Alternatively, an optical signal may be read by system 200. In this case, data transmission module 225 has an optical receptor that can receive a series of light pulses that represent a command—such as a command to turn off speaker 230.

Figure 3:
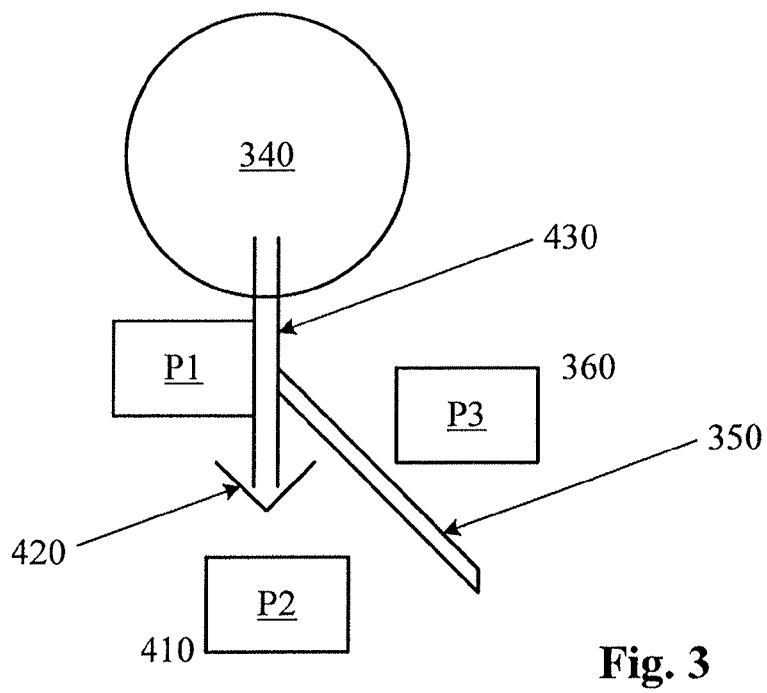
FIG. 3 is a diagram of an IOP sensor according to the principles of the present invention.

FIG. 3 is a diagram of an IOP sensor according to the principles of the present invention. In FIG. 3, the IOP sensor consists of three pressure sensors, P1, P2, and P3, a drainage tube 430, valve 420, and divider 350. Pressure sensor P1 is located in or is in fluidic communication with the anterior chamber 340, pressure sensor P2 is located at a drainage site in the subconjunctival space, and pressure sensor P3 is located remotely from P1 and P2. Pressure sensor P1 can also be located in a lumen or tube that is in fluid communication with the anterior chamber. As such, pressure sensor P1 measures a pressure in the anterior chamber, pressure sensor P2 measures a pressure at a drainage site, and pressure sensor P3 generally measures or corresponds to atmospheric pressure.

In FIG. 3, tube 430 drains aqueous from the anterior chamber 340 of the eye. A valve 420 controls the flow of aqueous through the tube 430. Pressure sensor P1 measures the pressure in the tube 430 upstream from the valve 420 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

A divider 350 separates pressure sensor P2 from pressure sensor P3. Pressure sensor P2 is located at a drainage site (e.g. 410 in FIG. 4). As such, pressure sensor P2 is located in a pocket that generally contains aqueous—it is in a wet location 410. Pressure sensor P3 is physically separated from pressure sensor P2 by divider 350. Divider 350 is a physical structure that separates the wet location 410 of P2 from the dry location 360 of P3. Divider 350 is included when the system of the present invention is located on a single substrate. In this configuration, all three pressure sensors (P1, P2, and P3) are located on a substrate that includes tube 430, valve 420, divider 350, and the other components of the system.

In one embodiment of the present invention, pressure sensor P3 is located in close proximity to the eye. Pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. P3 may also be located in a dry portion 360 of the subconjunctival space, separate from the drainage location. Regardless of location, pressure sensor P3 is intended to measure atmospheric pressure in the vicinity of the eye or at the eye's surface.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more. In addition, the effective atmospheric pressure can vary significantly—in excess of 100 mmHg—if a patient goes swimming, hiking, riding in airplane, etc. Such a variation in atmospheric pressure is significant since IOP is typically in the range of about 15 mm Hg. Thus, for 24 hour monitoring of IOP, it is desirable to have pressure readings for the anterior chamber (as measured by P1) and atmospheric pressure in the vicinity of the eye (as measured by P3).

Therefore, in one embodiment of the present invention, pressure readings are taken by P1 and P3 simultaneously or nearly simultaneously over time so that the actual IOP can be calculated (as P1−P3 or P1−f(P3)). The pressure readings of P1 and P3 can be stored in memory 220 by processor 215. They can later be read from memory so that actual IOP over time can be interpreted by a physician.

Pressure sensors P1, P2, and P3 can be any type of pressure sensor suitable for implantation in the eye. They each may be the same type of pressure sensor, or they may be different types of pressure sensors. For example, pressure sensors P1 and P2 may be the same type of pressure sensor (implanted in the eye), and pressure sensor P3 may be a different type of pressure sensor (in the vicinity of the eye).

Figure 4:
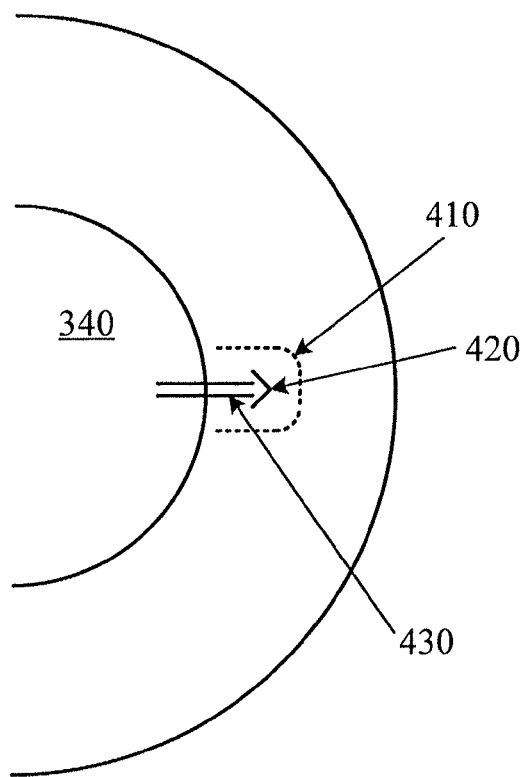
FIG. 4 is a diagram of one possible application of the IOP sensor of the present invention.

In another embodiment of the present invention, pressure readings taken by pressure sensors P1 and P2 can be used to control a device that drains aqueous from the anterior chamber 340. FIG. 4 is a diagram of one possible application of the IOP sensor of the present invention that utilizes the readings of pressures sensors P1 and P2. In FIG. 4, pressure sensor P1 measures the pressure in the anterior chamber 340 of the eye. Pressure sensor P2 measures the pressure at a drainage site 410.

Numerous devices have been developed to drain aqueous from the anterior chamber 340 to control glaucoma. Most of these devices are variations of a tube that shunts aqueous from the anterior chamber 340 to a drainage location 410. For example, tubes have been developed that shunt aqueous from the anterior chamber 340 to the subconjunctival space thus forming a bleb under the conjunctiva or to the subscleral space thus forming a bleb under the sclera. (Note that a bleb is a pocket of fluid that forms under the conjunctiva or sclera). Other tube designs shunt aqueous from the anterior chamber to the suprachoroidal space, the supraciliary space, the juxta-uveal space, or to the choroid. In other applications, tubes shunt aqueous from the anterior chamber to Schlemm's canal, a collector channel in Schlemm's canal, or any of a number of different blood vessels like an episcleral vein. Some tubes even shunt aqueous from the anterior chamber to outside the conjunctiva. Finally, in some applications, no tube is used at all. For example, in a trabeculectomy (or other type of filtering procedure), a small hole is made from the subconjunctival or subscleral space to the anterior chamber. In this manner, aqueous drains from the anterior chamber, through the hole, and to a bleb under the conjunctiva or sclera. Each of these different anatomical locations to which aqueous is shunted is an example of a drainage location 410.

In FIG. 4, a tube 430 with a valve 420 on one end is located with one end in the anterior chamber 340 and the other end in a drainage location 410. In this manner, the tube 430 drains aqueous from the anterior chamber 340 to the drainage location 410. Valve 420 controls the flow of aqueous from anterior chamber 340 to drainage location 410. Pressure sensor P1 is located in the anterior chamber or in fluid communication with the anterior chamber 340. As shown in the embodiment of FIG. 3, pressure sensor P1 is located upstream from valve 420. In this manner, pressure sensor P1 is located in the subconjunctival space but is in fluid communication with the anterior chamber 340.

Since pressure sensor P1 measures the pressure in the anterior chamber 340 and pressure sensor P2 measures pressure at the drainage location 410, the difference between the readings taken by these two pressure sensors (P1-P2) provides an indication of the pressure differential between the anterior chamber 340 and the drainage location 410. In one embodiment, this pressure differential dictates the rate of aqueous flow from the anterior chamber 340 to the drainage location 410.

One complication involved with filtering surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensor P1 and pressure sensor P2 can be used to control the flow rate through tube 430 by controlling valve 420. For example, valve 420 can be controlled based on the pressure readings from pressure sensor P1 and pressure sensor P2.

In another embodiment of the present invention, IOP (based on readings from pressure sensor P1 and pressure sensor P3) can be controlled by controlling valve 420. In this manner, IOP is the control parameter. Valve 420 can be adjusted to maintain a particular IOP (like an IOP of 15 mm Hg). Valve 420 may be opened more at night than during the day to maintain a particular IOP. In other embodiments, an IOP drop can be controlled. Immediately after filtering surgery, IOP can drop precipitously. Valve 420 can be adjusted to permit a gradual drop in IOP based on readings from pressure sensors P1 and P3.

In another embodiment of the present invention, readings from pressure sensor P2 (or from the difference between pressure sensor P2 and atmospheric pressure as measured by P3) can be used to control valve 420 so as to control the morphology of a bleb. One of the problems associated with filtering surgery is bleb failure. A bleb can fail due to poor formation or fibrosis. The pressure in the bleb is one factor that determines bleb morphology. Too much pressure can cause a bleb to migrate to an undesirable location or can lead to fibrosis. The pressure of the bleb can be controlled by using the reading from pressure sensor P2 (at drainage location 410—in this case, a bleb). In one embodiment of the present invention, the difference between the pressure in the bleb (as measured by P2) and atmospheric pressure (as measured by P3) can be used to control valve 420 to maintain a desired bleb pressure. In this manner, the IOP pressure sensor of the present invention can also be used to properly maintain a bleb.

Valve 420 can be controlled by microprocessor 215 or a suitable PID controller. A desired pressure differential (that corresponds to a desired flow rate) can be maintained by controlling the operation of valve 420. Likewise, a desired IOP, IOP change rate, or bleb pressure can be controlled by controlling the operation of valve 420.

While valve 420 is depicted as a valve, it can be any of a number of different flow control structures that meter, restrict, or permit the flow of aqueous from the anterior chamber 340 to the drainage location 410. In addition, valve 420 can be located anywhere in or along tube 430.

Finally, there are many other similar uses for the present IOP sensor. For example, various pressure readings can be used to determine if tube 420 is occluded or obstructed in some undesirable manner. As such, failure of a drainage device can be detected. In a self clearing lumen that shunts the anterior chamber 340 to a drainage location 410, an undesirable blockage can be cleared based on the pressure readings of P1, P2, and/or P3.

FIG. 5 is an end cap implementation of an IOP sensor consistent with the principles of the present invention. In FIG. 5, pressure sensors P1 and P3 are integrated into an end cap 510. End cap 510 fits in tube 430 so as to form a fluid tight seal. One end of tube 430 resides in the anterior chamber 340, and the other end of tube 430 (where end cap 510 is located) is located outside of the anterior chamber 340. Typically, on end of tube 430 resides in the anterior chamber 340, and the other end resides in the subconjunctival space. In this manner, pressure sensor P1 is in fluid communication with the anterior chamber 340. Since there is almost no pressure difference between the anterior chamber 340 and the interior of tube 430 that is in fluid contact with the anterior chamber 340, pressure sensor P1 measures the pressure in the anterior chamber 340. Pressure sensor P3 is external to the anterior chamber 340 and either measures atmospheric pressure or can be correlated to atmospheric pressure.

Typically, tube 430 is placed in the eye to bridge the anterior chamber 340 to the subconjunctival space, as in glaucoma filtration surgery. In this case, P3 resides in the subconjunctival space. In this configuration, P3 measures a pressure that is either very close to atmospheric pressure or that can be correlated to atmospheric pressure through the use of a simple function. Since plug 510 provides a fluid tight seal for tube 430, pressure sensor P3 is isolated from pressure sensor P1. Therefore, an accurate IOP reading can be taken as the difference between the pressure readings of P1 and P3 (P1−P3). In one embodiment, a single, thin membrane 520—typically a piezoresistive crystal—resides in the sensor package and is exposed to P1 on one side (tube side) and P3 on the other side (isolation side), and thus the net pressure on the membrane 520 is recorded by the sensor, providing a gauge reading corresponding IOP.

FIGS. 6A and 6B are perspective views of the end cap implementation of FIG. 5. In this embodiment, pressure sensor P1 is located on one end of end cap 510 so that it can be located inside tube 430. Pressure sensor P3 is located on the other end of end cap 510 so that it can be located outside of tube 430. A membrane (520) separates P1 from P3. In this manner, pressure sensor P1 is isolated from pressure sensor P3. While pressure sensors P1 and P3 are depicted as being located on opposite surfaces of a membrane 520 in the end cap 510, they can also be located integral with end cap 510 in any suitable position to facilitate the pressure measurements.

Figure 7A:
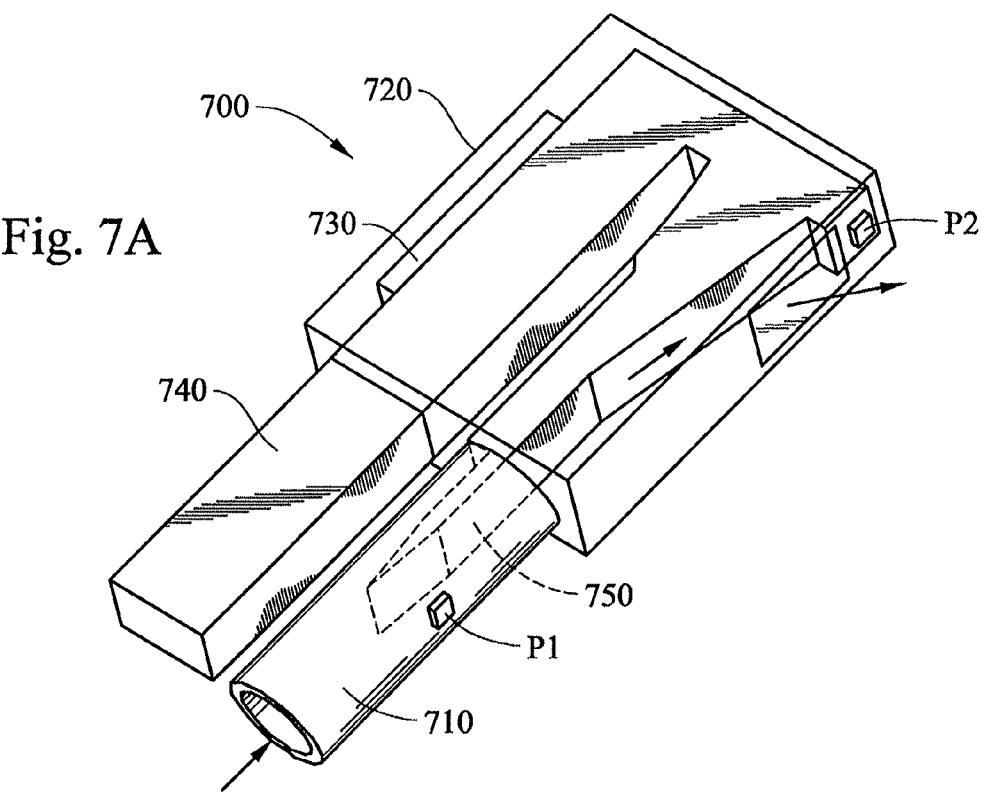
FIGS. 7A and 7B are perspective views of a lumen clearing valve according to the principles of the present invention.
Figure 7B:
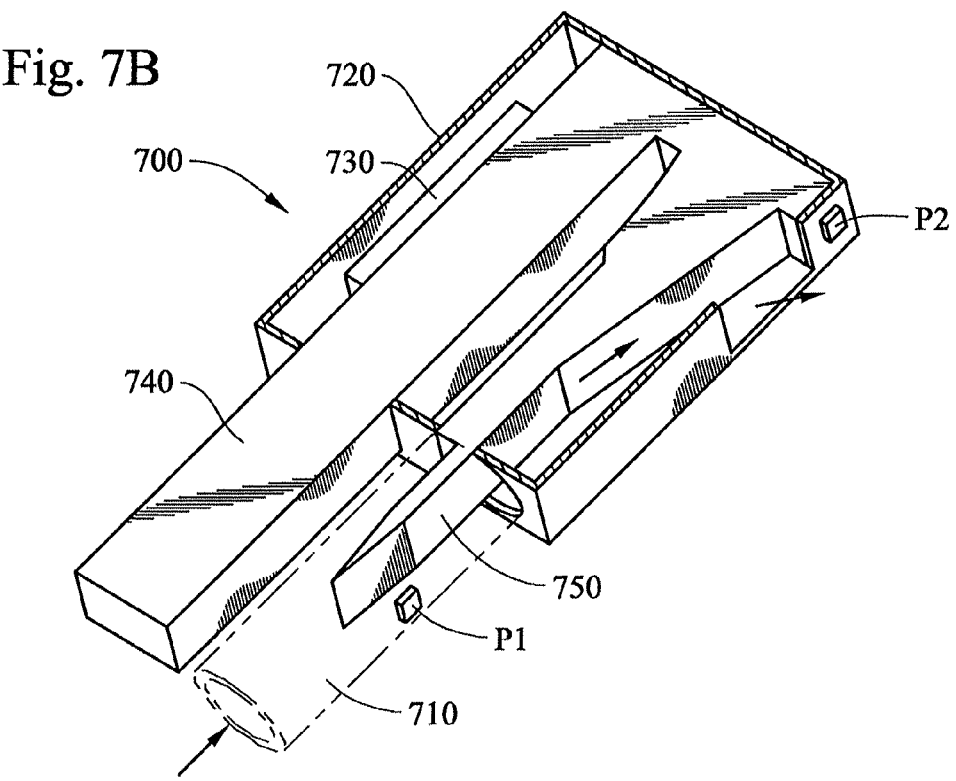

FIGS. 7A and 7B are perspective views of a lumen clearing valve according to the principles of the present invention, which can serve as control valve 420. In FIGS. 7A and 7B, the lumen clearing valve 700 includes tube 710, housing 720, actuator 730, actuation arm 740, tapered arm 750, pressure sensor P1, and pressure sensor P2. As previously described with reference to FIGS. 3 and 4, one end of tube 710 is located in the anterior chamber and the other end of tube 710 is coupled to housing 720. Pressure sensor P1 monitors the pressure in the anterior chamber. Actuator 730 is located in housing 720. Actuator 730 is coupled to actuation arm 740 which in turn is rigidly connected to tapered arm 750. Tapered arm 750 is configured to extend into the lumen of tube 710. Pressure sensor P2 is located at the outflow region of housing 720 (i.e. in the drainage location). The arrows denote the flow of aqueous from the anterior chamber to the drainage location.

Housing 720 is generally flat but may have a slight curvature that accommodates the curvature of the eye. Housing 720 holds actuator 730. Housing 720 also holds the actuation arm 740 and tapered arm 750. Tube 710 is fluidly coupled to a channel located in the interior of housing 720. This channel conducts aqueous from the anterior chamber (through tube 710) and to the drainage location. Housing 720 can be made of any of a number of different biocompatible materials such as stainless steel.

Actuator 730 moves actuation arm 740 back and forth in a plane. In this manner, actuation arm 740 oscillates or reciprocates when a force is applied on it by actuator 730. Since tapered arm 750 is rigidly coupled to actuation arm 740, it also oscillates or reciprocates in tube 710. Actuator 730 can be based any of a number of different known methods such as electromagnetic actuation, electrostatic actuation, piezoelectric actuation, or actuation by shape memory alloy materials. Actuation arm 740 can be moved by actuator 730 at a low repetition rate (for example, a few Hertz) or a high actuation rate (for example, ultrasonic).

Tapered arm 750 is sized to fit in tube 710. In this manner, tapered arm 750 can be made to oscillate back and forth in tube 710 to clear any material that is blocking tube 710. Tapered arm 750 has a generally pointed end that is located in tube 710. As shown, tapered arm 750 also has a larger tapered portion that can serve to restrict flow through tube 710 thus functioning as a valve. In this manner, not only can tapered arm 750 be oscillated to clear material blocking tube 710, but it can also be moved to a position that partially obstructs flow through tube 710. The tapered designed of arm 750 allows for a variable level of flow restriction through tube 710 by the varying the position of arm 750 relative to housing 720 and tube 710.

When used as a valve, tapered arm 750 can restrict the amount of aqueous that enters the drainage location and exits the anterior chamber. Controlling aqueous flow can reduce the chances of hypotony after filtration surgery, maintain a suitable IOP, and control the amount of stagnant aqueous in the drainage location. When the drainage location is a subconjunctival bleb, controlling the amount of stagnant aqueous in the bleb can help maintain proper bleb morphology and reduce the amount of fibrosis. Too much stagnant aqueous in a bleb can lead to fibrosis. It has been postulated that fibroblasts form in stagnant aqueous and that too much tension on the bleb wall (i.e. too high a pressure in the bleb) can lead to bleb failure. The use of tapered arm 750 as a valve, therefore, can lead to proper bleb maintenance which decreases the chances of these deleterious side effects.

The lumen clearing valve system 700 can be controlled based on readings from P1, P2, and P3 as described above. The lumen clearing valve system 700 of the present invention can be made using a MEMS process in which layers are deposited on a substrate that forms part of housing 720. All of the elements of the lumen clearing valve system 700 can be located on, under, or embedded in a plate that extends into the drainage location—much like currently available glaucoma drainage devices.

FIG. 8 is a perspective view of a lumen clearing valve with a fiber clearing member according to the principles of the present invention. The embodiment of FIG. 8 is similar to that of FIG. 7, except that FIG. 8 also depicts a needle head 810 that is located in the drainage location. Typically, the drainage location is in the subconjunctival space. In this manner, a bleb in the subconjunctival space receives the aqueous that exits the housing 710. Needle head 810 can be oscillated to keep the bleb clear of fibers or to reduce fibrosis (which is one cause of bleb failure). In this manner, when actuation arm 740 is moved, needle head 810 is moved in the drainage location (in this case, a bleb). Needle head 810 can dislodge fibers and prevent the build up of fibrotic tissue.

FIG. 9 is a perspective view of a lumen clearing valve with an aqueous dispersion member to clear fibrosis according to the principles of the present invention. The embodiment of FIG. 9 is similar to that of FIG. 7, except that FIG. 9 also depicts a needle head 910 that is located in the drainage location. In this embodiment, needle head 910 may serve to clear fibers in the drainage location and/or disperse aqueous to the drainage location. The outlet end of housing 920 is open to allow aqueous to flow to the drainage location. Needle head 910 is located near the outlet within the housing. Needle head 910 is generally broad and blunt so that when it oscillates, aqueous is distributed to the drainage location. Fluid passes from tube 710 to the drainage location via microchannels 930, which are typically etched into needle head 910. The dispersion of aqueous can help reduce the formation of resistance at the drainage location, typically created by bleb formation and/or fibrotic growth, by providing a larger effective area in the drainage location, decreasing bleb height, and/or reducing bleb pressure in order to more properly manage bleb morphology. Additionally, the dispersion of aqueous can aid the flow of drainage by providing a mechanical means of overcoming the flow resistance associated with the drainage location, typically created by bleb formation and/or fibrotic growth.

Figure 10:
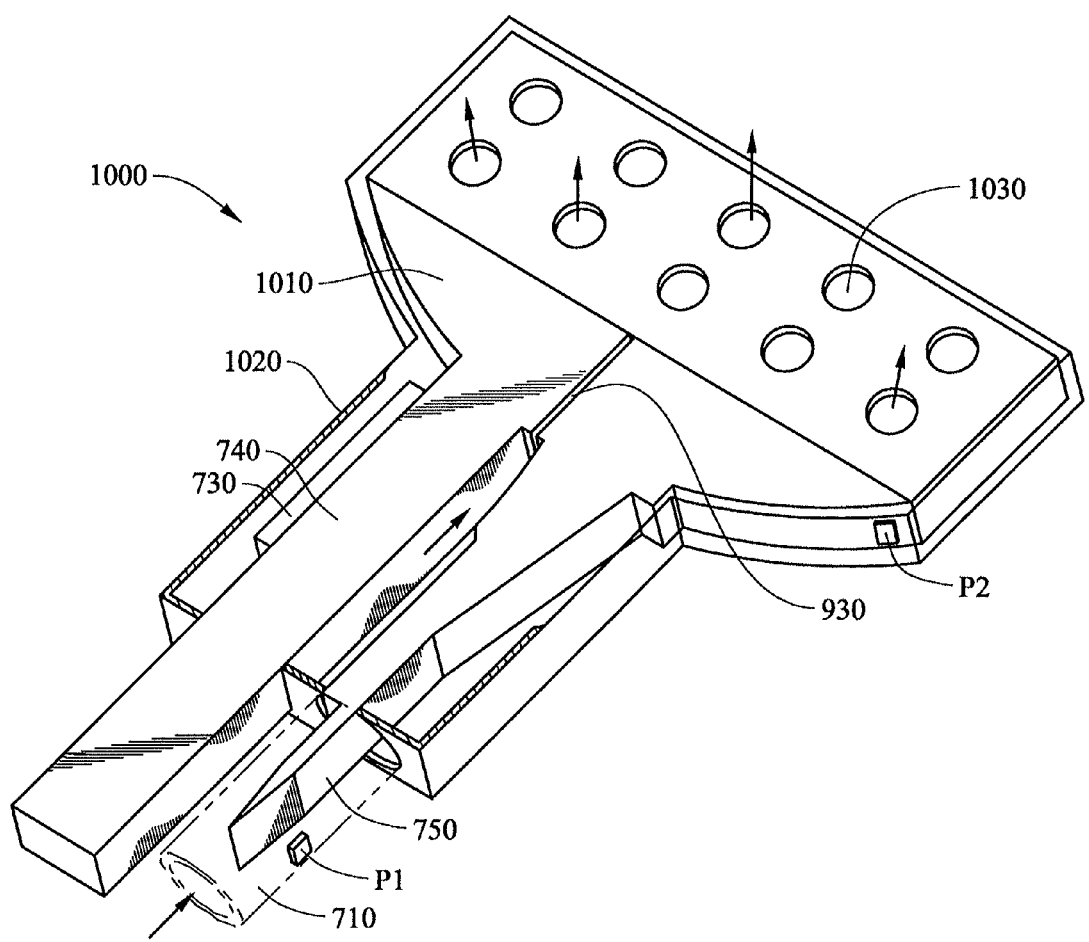
FIG. 10 is a perspective view of a lumen clearing valve with hybrid external member according to the principles of the present invention.

FIG. 10 is a perspective view of a lumen clearing valve with hybrid external member according to the principles of the present invention. The embodiment of FIG. 10 is similar to the embodiment of FIG. 9. In FIG. 10, a broad needle head 1010 and additional drainage holes 1030 allow for a wide dispersion of aqueous in the drainage location (typically, a subconjunctival bleb). Fluid passes from tube 710 to the drainage location via microchannels 930, which are typically etched into needle head 1010. In FIG. 10, housing 1020 has a broad outlet end that includes multiple drainage holes 1030. In addition, the broad end of housing 1020 is open to allow aqueous to flow through this wide opening. Therefore, in the embodiment of FIG. 10, aqueous flows from the anterior chamber through tube 710, through housing 1020 and out of drainage holes 1030 and the broad end of housing 1020 into the drainage location. When needle head 1010 is oscillated, it can serve to clear fibers from the drainage location. It can also disperse aqueous to the drainage location.

The embodiments of FIGS. 7-10 can be operated in two different modes—lumen clearing mode in which the tapered arm 750 oscillates or moves and valve mode in which the tapered arm 750 is maintained in a particular position to restrict fluid flow through tube 710. In lumen clearing mode, tapered arm 750 is moved or oscillated to clear fibrous material from the interior of tube 710 and/or the drainage location. In lumen clearing mode, tapered arm 750 can also help to disperse aqueous in the drainage location.

When operating as a valve, tapered arm 750 can be maintained in a particular position to restrict the flow of aqueous through tube 710. The position of tapered arm 750 can be changed over time based on pressure readings from pressure sensors P1, P2, and/or P3 as described above with respect to FIGS. 3-6. In this manner, any of the following can be the basis for control of the tapered arm 750: IOP, pressure in the bleb, fluid flow rate, etc.

Figure 11A:
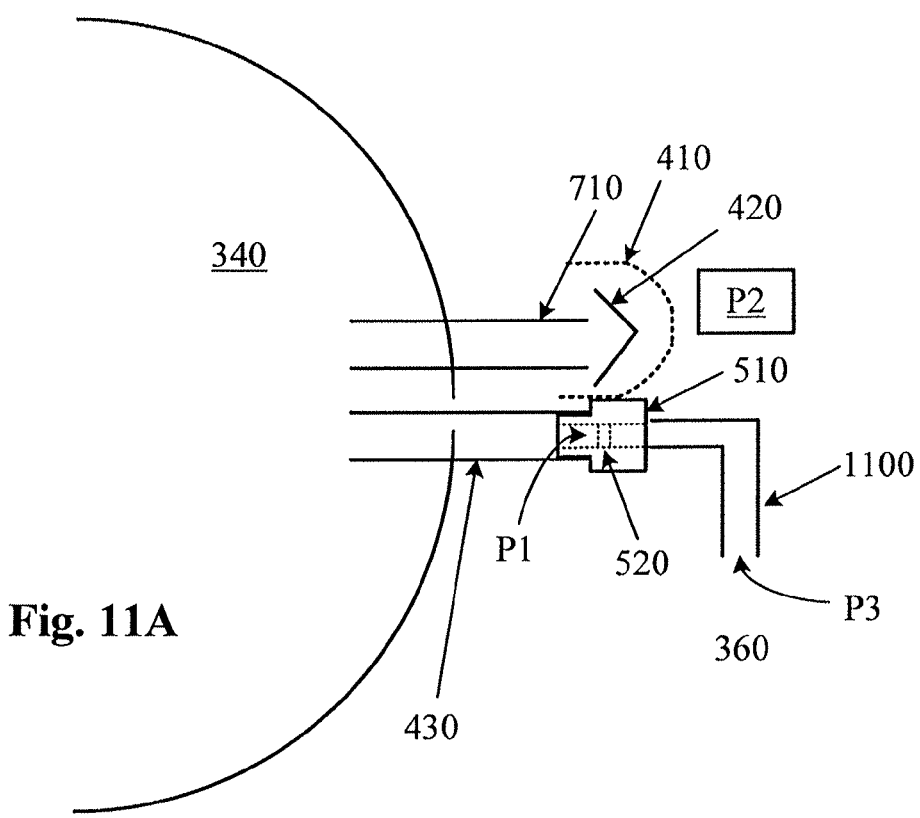
FIGS. 11A and 11B depict an end cap implementation of the valve and pressure sensor system according to the principles of the present invention that includes both single and dual lumen versions.
Figure 11B:
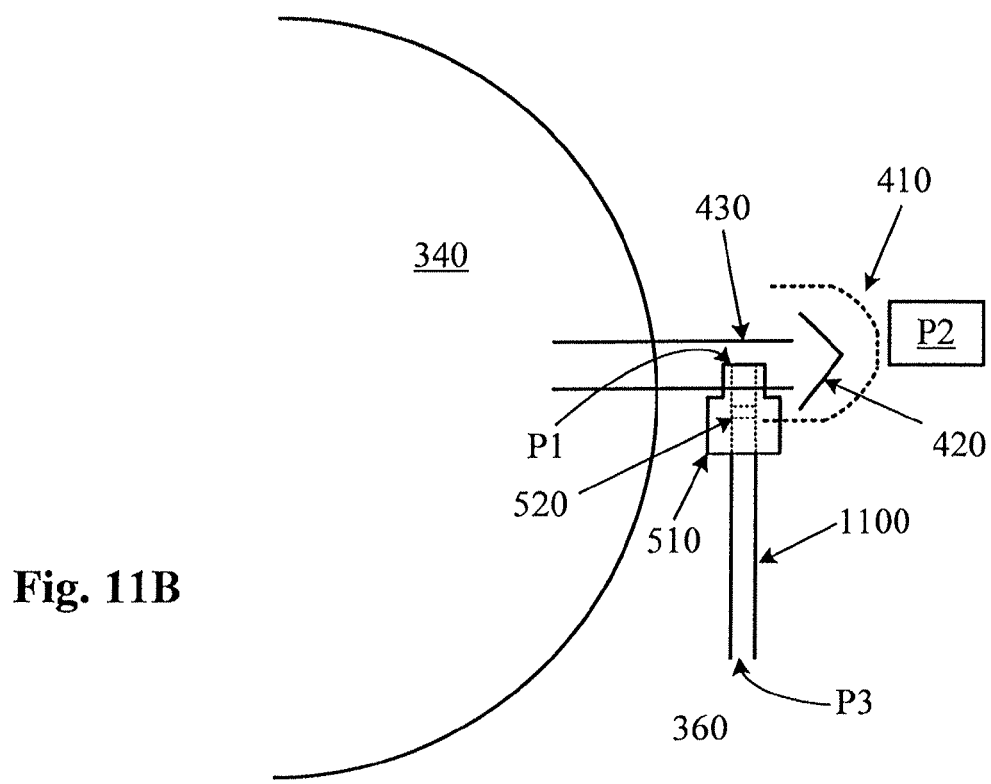

FIG. 11A is a diagram of a two lumen valve and pressure sensor system according to the principles of the present invention. In FIG. 11A, tube 710 of the active valve/lumen clearing system bridges the anterior chamber and a drainage location. A second tube 430 includes end cap 510 as described in FIG. 5. The system of FIG. 11A combines the pressure sensor of FIGS. 5 and 6 with the active valve/lumen clearing device of FIGS. 7-10, wherein the latter can serve as control valve 420. In this manner, one tube (430) can be used to measure IOP, while a second tube (710) can be used for draining aqueous. Fluidic communication between a dry location 360 and the P3 sensing portion of end cap 510 can be provided by tube 1100. FIG. 11B is another possible arrangement, wherein a single tube resides in the anterior chamber 340. In FIG. 11B, end cap 510 is located in an opening in tube 430.

Figure 12A:
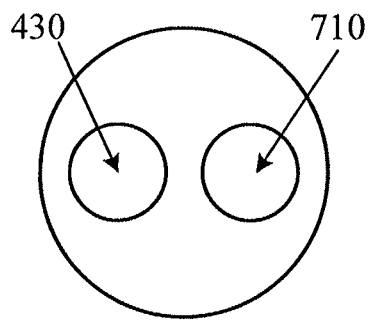
FIGS. 12A and 12B are cross section views of dual tubing that can be used with the system of the present invention.
Figure 12B:
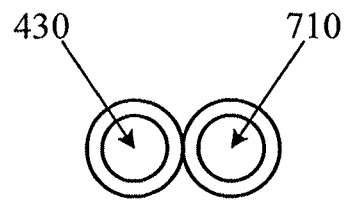

FIGS. 12A and 12B are cross section views of dual tubing that can be used with the system of the present invention. In FIG. 12A, two lumens, 430 and 710, are contained in a single tube. FIG. 12A shows this dual bore tubing arrangement. In FIG. 12B, two lumens, 430 and 710, are contained in two separate tubes that are joined together. FIG. 12B shows this dual-line tubing arrangement. Other variations of a dual lumen device can also be used in conjunction with the present invention.

Figure 13:
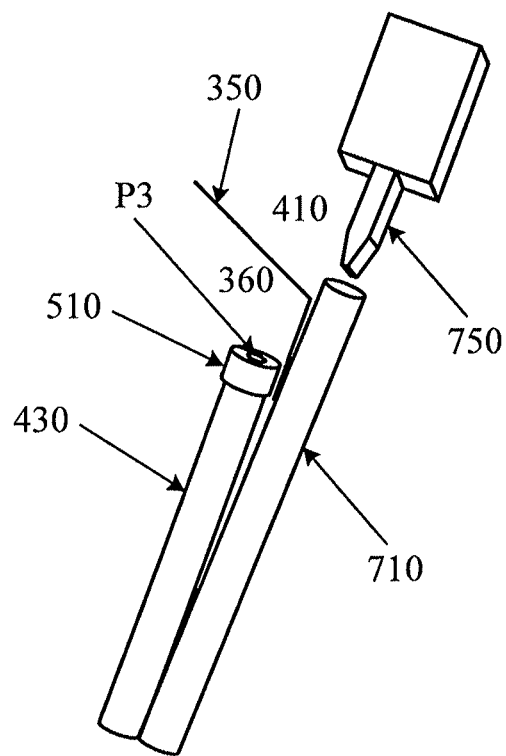
FIG. 13 is a perspective view of a two lumen valve and pressure sensor system according to the principles of the present invention.

FIG. 13 is a perspective view of a two lumen valve and pressure sensor system according to the principles of the present invention. In FIG. 13, two tubes, 430 and 710, are connected at one end (the end that resides in the anterior chamber) and are separated at the other end (in this case, the end that resides in the subconjunctival space). Tube 430 has end cap 510 that measures IOP. Tube 710 receives tapered arm 750. Tapered arm 750 can serve to clear the interior of tube 710. Tube 750 can also act as a valve that can partially or totally occlude the interior of tube 710. Tapered arm 750 is coupled to the any of the systems depicted in FIGS. 7-10. A barrier 350 separates P3 from the outlet of 710, typically the drainage location 410. In this manner, P3 is in a "dry" space 360 and measures an approximation of atmospheric pressure. The outlet end of 710 (shown adjacent to tapered arm 750) is located in a "wet" space or drainage location such as 410. As noted above, P2 is located in this "wet" space.

Figure 14:
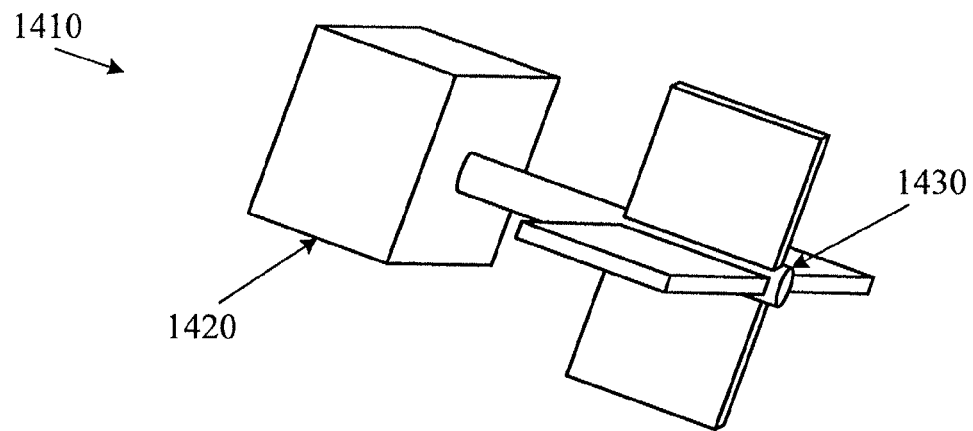
FIG. 14 is a perspective view of power generator according to the principles of the present invention.

Power for the pressure monitoring system or active drainage system may be supplied by a power source 205 as described above. As shown in FIG. 2, power source 205 is coupled to power generator 1410. One example of power generator 1410 is shown in FIG. 14. In FIG. 14, power generator 1410 has a micro-generator 1420 coupled to a rotor 1430. In this example, as rotor 1430 turns, micro-generator 1420 produces power. As such, the operation of power generator 1410 is much like that of any conventional generator. While rotor 1430 is shown as having four paddles connected to a shaft, any rotor design may be employed. Moreover, any other type of apparatus that converts a fluid flow into power may be employed. FIG. 14 is intended only as one example.

Power generator 1410 is capable of harnessing the aqueous fluid flow from the anterior chamber 340 to the drainage location 410. Since the general purpose of any glaucoma drainage device is to shunt aqueous from the anterior chamber 340 to a drainage location 410, aqueous flows from the anterior chamber 340 to the drainage location 410 (in this case, through a tube, such as tube 430). There is a natural pressure difference between the fluid pressure in the anterior chamber 340 and the fluid pressure in the drainage location 410. This pressure difference causes aqueous to flow from the anterior chamber 340 to the drainage location 410. Power generator 1410 converts this aqueous fluid flow into power.

In a typical example, the aqueous flowing through the tube 430 turns rotor 1430 at about 1 revolution per minute based on an aqueous flow rate of about two microliters per minute. If the pressure difference between the anterior chamber 340 and the drainage location 410 is about eight millimeters of mercury, the transferable potential power is about 25 nanowatts (or about two milliJoules of energy) per day. This power can be stored in power source 205 and used to power the systems (pressure sensors, telemetry, active valve, etc.) described in this application.

Figure 15:
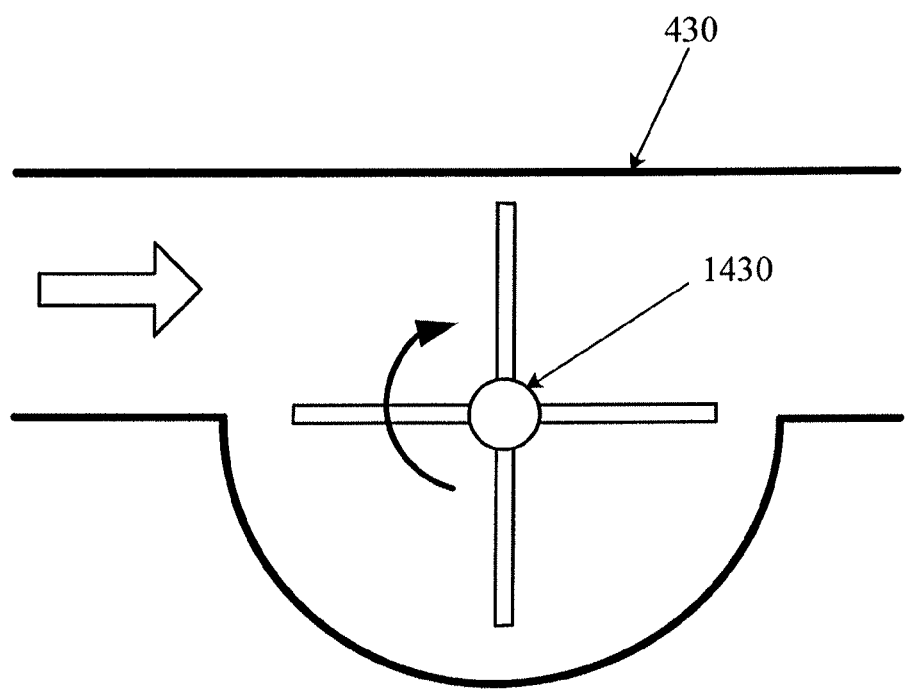
FIG. 15 is an end view of a rotor located in a tube according to the principles of the present invention.

FIG. 15 is an end view of one embodiment of a rotor according to the principles of the present invention. In FIG. 15, rotor 1430 has a shaft connected to four paddles. Rotor 1430 is located in tube 430 to harness the fluid flowing through the tube. The arrows denote the direction of aqueous fluid flow through tube 430 and the corresponding direction of rotation of rotor 1430. As noted, FIG. 15 depicts one of many possible configurations for rotor 1430.

Figure 16:
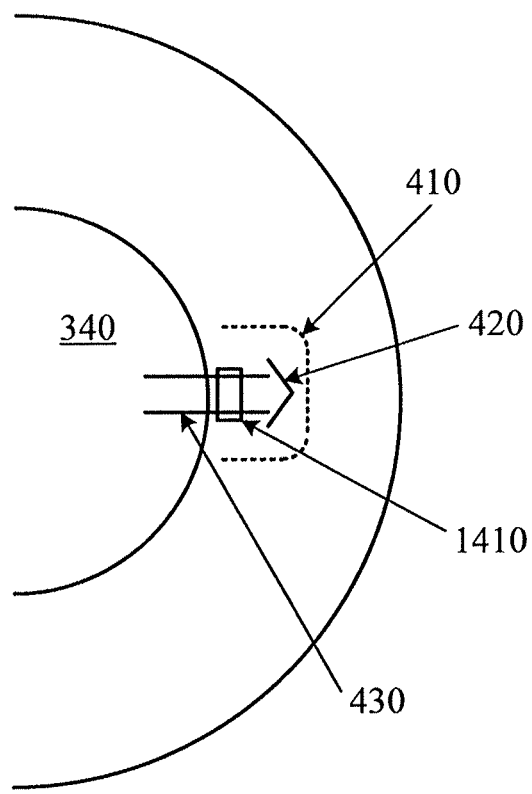
FIG. 16 is a diagram of one possible location of a power generator in a glaucoma drainage system according to the principles of the present invention.

FIG. 16 is a diagram of one possible location of a power generator in a glaucoma drainage system according to the principles of the present invention. In the example of FIG. 16, power generator 1410 is located in or along tube 430. Tube 430 shunts the anterior chamber 340 to the drainage location 410. Valve 420 is located at the end of tube 430 as previously described. In this example, the power generated by power generator 1410 is used to power valve 420 (and other components of the system).

Figure 17:
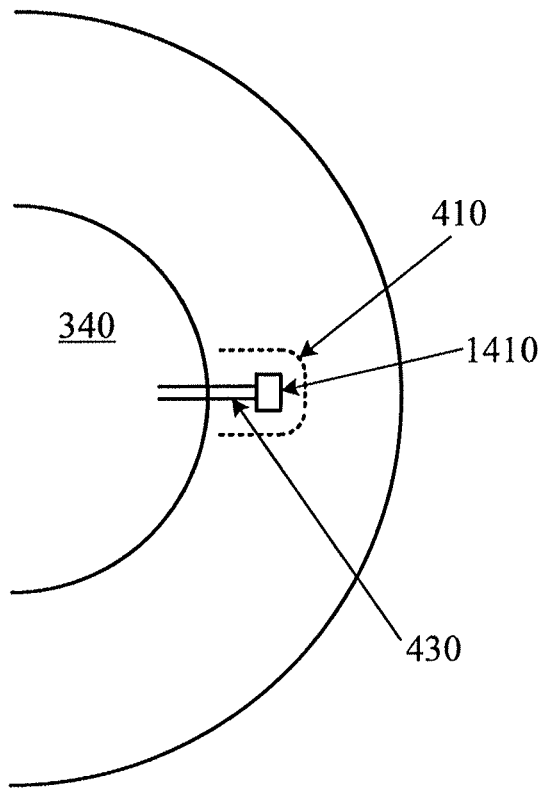
FIG. 17 is a diagram of another possible location of a power generator in a glaucoma drainage system according to the principles of the present invention.

FIG. 17 is a diagram of another possible location of a power generator in a glaucoma drainage system according to the principles of the present invention. In the example of FIG. 17, power generator 1410 is located at the end of tube 430. Here, power generator 1410 performs two functions: it generates power and it acts as a valve. Since power generator 1410 resists the flow of fluid through tube 430, this flow resistance can be used to control the rate of aqueous flowing through tube 430. In other words, power generator 1410 can be operated as an active valve. Moreover, the rotation of the rotor can function to clear the lumen (as described above).

In the example of FIG. 17, the micro-generator 1420 can be controlled to vary the flow resistance of rotor 1430. When micro-generator 1420 is a simple magnetic core and coil generator (like the typical electric generator), the distance between the magnetic core and the coil can be varied to vary the force required to turn rotor 1430. The more force required to turn rotor 1430, the more resistance to aqueous flowing through tube 430. Conversely, the less force required to turn rotor 1430, the less resistance to aqueous flowing through tube 430. This resistance to aqueous flow can be controlled to maintain a desired IOP.

Figure 18:
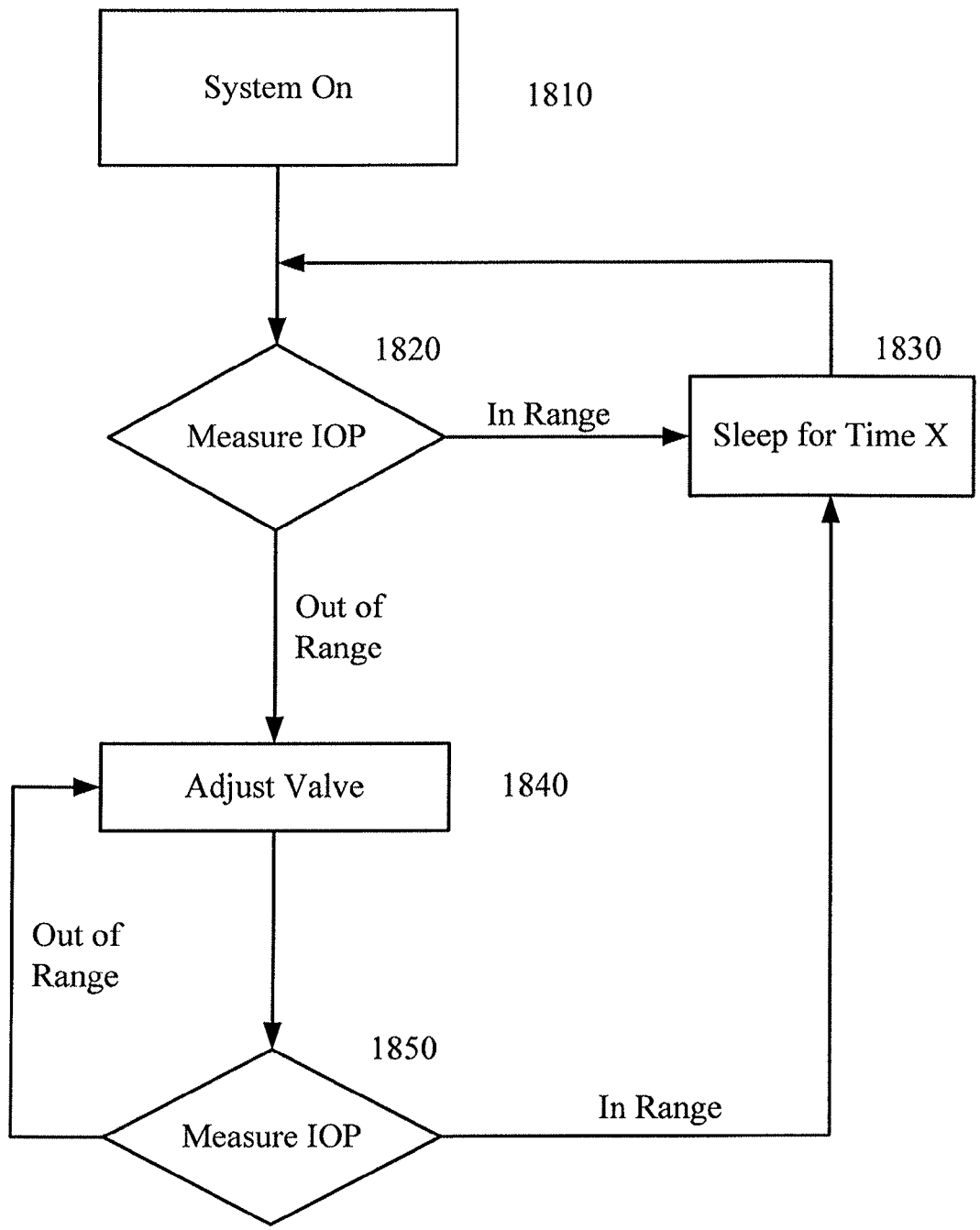
FIG. 18 is a flow chart of one method of operating the glaucoma drainage device of the present invention.

Regardless of whether the glaucoma drainage device has a power generator or operates on stored energy, a power savings method of operating the device may be beneficial. FIG. 18 is a flow chart of one method of operating the glaucoma drainage device of the present invention so as to conserve power. In 1810, the system is powered on. In 1820, IOP is measured. IOP may be measured as described above. If IOP is in range, then in 1830, the device powers off (i.e. is in sleep mode) for a time X. If IOP is out of range, then in 1840, the valve is adjusted accordingly. In 1850, IOP is measured. If IOP is in range, then in 1830, the device powers off (i.e. is in sleep mode) for a time X. If IOP is out of range, then in 1840, the valve is adjusted accordingly. This iterative process can be repeated as necessary to maintain IOP in a desired range.

Accordingly, with the operation depicted in FIG. 18, the glaucoma drainage device of the present invention takes periodic IOP measurements and makes adjustments accordingly. The time interval X between IOP measurements can be any time period. For example, IOP measurements can be made every ten minutes or every hour. A range of values can be set that determine whether the IOP readings are in range or out of range. For example, an IOP above 15 mm Hg may be considered too high. If an IOP measurement is taken that is above 15 mm Hg, it is out of range, and the valve is adjusted accordingly. The IOP measurement in 1850 may also be repeated at any time interval to adjust the valve. For example, the IOP reading in 1850 may be repeated every minute in the process of adjusting the valve.

From the above, it may be appreciated that the present invention provides a lumen clearing valve that can be controlled by an IOP sensor. The present invention provides a valve-like device that can clear a lumen, disperse aqueous, and/or clear fibrous material from a drainage location. The present invention also provides an implantable power generator that can be used to power such a system. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A glaucoma drainage device comprising:
    an active valve configured to be located between an anterior chamber of an eye and a drainage location;
    wherein the active valve comprises:
        a housing with an open outlet end on a first end of the housing, and a needle head opening on a second end of the housing;
        a tube in fluid communication with the open outlet end of the housing, the tube extending from the open outlet end of the housing;
        an actuator located in the housing;
        an actuation arm located at least partially in the housing, the actuation arm coupled to the actuator;
        a tapered arm rigidly coupled to the actuation arm such that movement of the actuation arm results in movement of the tapered arm and the needle head, a tapered end of the tapered arm located at least partially in the tube; and
        a needle head coupled to the actuation arm and the tapered arm, the needle head located opposite the tapered end of the tapered arm, the needle head located at least partially within the housing at the needle head opening of the housing;
    a power source coupled to the active valve; and
    a controller coupled to the power source;
    wherein the controller directs power from the power source to the active valve based on a pressure.

2. The glaucoma drainage device of claim 1 wherein the pressure is intraocular pressure and the controller directs power from the power source to the active valve when the intraocular pressure is not in a range.

3. The glaucoma drainage device of claim 1 wherein the drainage location is selected from the group consisting of: a subconjunctival space of the eye, a suprachoroidal space of the eye, a supraciliary space of the eye, a subscleral space of the eye, and outside the eye.

4. The glaucoma drainage device of claim 1 wherein the controller controls the position of the tapered arm so that it partially obstructs the tube thereby restricting fluid flow through the tube.

5. The glaucoma drainage device of claim 1 wherein the controller controls the actuator to move the needle head in a drainage location to disperse aqueous in the drainage location.

6. The glaucoma drainage device of claim 1 further comprising:
    a first pressure sensor located in fluid communication with an anterior chamber of an eye; and
    a second pressure sensor located in the drainage location;
    wherein a difference between readings from the first pressure sensor and the second pressure sensor approximates a pressure differential between the anterior chamber and the drainage location; and further wherein the controller uses the pressure differential to control the active valve.

7. The glaucoma drainage device of claim 4 further comprising:
    a first pressure sensor located in fluid communication with an anterior chamber of an eye; and
    a remote pressure sensor located remotely from the first pressure sensor such that the remote pressure sensor measures or approximates atmospheric pressure;
    wherein a difference between readings from the first pressure sensor and the remote pressure sensor approximates intraocular pressure; and further wherein the controller uses intraocular pressure to control the active valve.

8. An intraocular system comprising:
    a first pressure sensor located in fluid communication with an anterior chamber of an eye;
    a remote pressure sensor located remotely from the first pressure sensor such that the remote pressure sensor measures or approximates atmospheric pressure;
    a barrier that separates the first pressure sensor from the remote pressure sensor;

a controller configured to read the first and second pressure sensors; and a power source coupled to the controller; and an active valve comprising:
- a housing with an open outlet end on a first end of the housing, and a needle head opening on a second end of the housing;
- a tube in fluid communication with the open outlet end of the housing, the tube extending from the open outlet end of the housing;
- an actuation arm located at least partially in the housing, the actuation arm coupled to the actuator;
- a tapered arm rigidly coupled to the actuation arm such that movement of the actuation arm results in movement of the tapered arm and the needle head, a tapered end of the tapered arm located at least partially in the tube; and
- a needle head coupled to the actuation arm and the tapered arm, the needle head located opposite the tapered end of the tapered arm, the needle head located at least partially within the housing at the needle head opening of the housing;

wherein a difference between readings from the first pressure sensor and the remote pressure sensor approximates intraocular pressure; and further wherein the first pressure sensor, the remote pressure sensor, and the barrier are all located on a single device implantable in the eye.

* * * * *